United States Patent
Davila et al.

[11] Patent Number: 5,851,464
[45] Date of Patent: Dec. 22, 1998

[54] METHOD OF MAKING A FUSELESS SOFT TIP CATHETER

[75] Inventors: Luis A. Davila, Miami; Stephen J. Querns, Boca Raton; Mark Inderbitzen, Miramar, all of Fla.

[73] Assignee: Cordis Corporation, Miami Lakes, Fla.

[21] Appl. No.: 645,401

[22] Filed: May 13, 1996

[51] Int. Cl.[6] .......................... B29C 47/06; B29C 44/06
[52] U.S. Cl. ................ 264/103; 264/171.12; 264/171.27; 264/171.28; 264/173.14; 264/173.15; 264/209.3; 264/210.2
[58] Field of Search .............................. 264/103, 171.12, 264/171.16, 171.23, 171.24, 171.26, 171.28, 173.16, 173.19, 322, 296, 173.14, 173.15, 171.27, 209.3–210.2

[56] References Cited

U.S. PATENT DOCUMENTS

| | | | |
|---|---|---|---|
| 3,762,986 | 10/1973 | Bhuta et al. | 161/227 |
| 4,316,870 | 2/1982 | Rowley | 425/393 |
| 4,321,226 | 3/1982 | Markling | 264/139 |
| 4,551,292 | 11/1985 | Fletcher et al. | 264/139 |
| 4,596,563 | 6/1986 | Pande | 604/264 |
| 4,627,844 | 12/1986 | Schmitt | 604/264 |
| 4,636,346 | 1/1987 | Gold et al. | 264/139 |
| 4,705,511 | 11/1987 | Kocak | 604/282 |
| 4,764,324 | 8/1988 | Burnham | 264/103 |
| 4,790,831 | 12/1988 | Skribiski | 604/282 |
| 4,948,643 | 8/1990 | Mueller | 428/36.6 |
| 5,226,899 | 7/1993 | Lee et al. | 604/282 |
| 5,318,032 | 6/1994 | Lonsbury et al. | 604/282 |
| 5,403,292 | 4/1995 | Ju | 604/282 |
| 5,439,454 | 8/1995 | Lo et al. | 604/264 |
| 5,451,206 | 9/1995 | Young | 604/43 |
| 5,451,209 | 9/1995 | Ainsworth et al. | 604/282 |
| 5,468,221 | 11/1995 | Schoner | 604/264 |
| 5,484,565 | 1/1996 | Larsen et al. | 264/230 |
| 5,554,139 | 9/1996 | Okajima | 604/282 |
| 5,599,325 | 2/1997 | Ju et al. | 604/282 |
| 5,614,136 | 3/1997 | Pepin et al. | 264/40.3 |
| 5,662,665 | 9/1997 | Wang | 264/150 |
| 5,667,499 | 9/1997 | Welch et al. | 604/282 |

FOREIGN PATENT DOCUMENTS

| | | |
|---|---|---|
| 0363953 | 10/1989 | European Pat. Off. . |
| 0618059 | 4/1994 | European Pat. Off. . |
| 16570 | 2/1977 | Japan . |
| WO 93/08861 | 5/1993 | WIPO . |

*Primary Examiner*—Jan H. Silbaugh
*Assistant Examiner*—Mark Eashoo
*Attorney, Agent, or Firm*—Dean Garner

[57] ABSTRACT

A catheter having an elongated tubular body with a distal end, a proximal end and at least one lumen extending therebetween. The body is made from three layers of extruded plastic which adhere to each other. The body has an inner and outer layer made from a polymer, and a middle layer also made from a polymer. The middle layer is more flexible and has a lower melt temperature than the inner and outer layers. The catheter further includes an integral fuseless distal tip. The distal tip is made from the middle layer and no more than one of the inner and outer layers. The distal tip is softer than portions of the body proximal thereto. In accordance with another aspect of the present invention, there is provided a method of making a fuseless soft tip tubular catheter, of the type described above. The method involves extruding the catheter so as to form the tubular body having the inner, outer and middle layers. Thereafter, at least the distal end of the catheter is heated so as to form a distal tip. The distal tip is made from the middle layer and no more than one of the inner and outer layers. The distal tip is softer than portions of said body proximal thereto.

8 Claims, 4 Drawing Sheets

METHOD OF MAKING A FUSELESS SOFT TIP CATHETER

FIELD OF THE INVENTION

The present invention relates to medical catheters, such as guiding catheters and angiographic catheters. The present invention has even further relation to such a catheter that has a soft distal tip which is integral with the body of the catheter and does not have to be fused thereon. The present invention has even further relation to a method of making such a catheter.

BACKGROUND OF THE INVENTION

Catheters such as intravascular catheters are well known for use in diagnostic and therapeutic applications where it is necessary to administer a fluid to, or otherwise contact, a precise location within the cardiovascular system, for example, by guiding the tip or distal end of the catheter through branching blood vessels. Such guiding is accomplished in part by manipulation of a proximal portion of the catheter in order to impart forces needed to curve and guide the catheter through the curving and branching blood vessels.

Because these types of catheters are used in an intravascular manner, they must have an extremely small outside diameter. Inasmuch as such catheters typically come into contact with living tissue, including organs such as the heart, it is extremely important that the catheter be in place for a minimal length of time. It is also important that these catheters be very resistant to the formation of kinks. This requires the catheter to possess a certain degree of stiffness, while at the same time possessing adequate flexibility to be responsive to maneuvering forces and to be as atraumatic as possible. Catheters that require a relatively stiff inner lumen can advantageously utilize these properties. Included are intravascular catheters, guiding catheters through which balloon catheters for angioplasty techniques and the like can be passed, and sheaths where wall thinness and strength are particularly important.

Such catheters are typically made from plastic and have a wire braid imbedded therein, to provide the necessary stiffness characteristics. Examples of such catheters are given in U.S. Pat. Nos. 3,585,707 issued to Stevens on Jun. 22, 1971 and 3,485,234 issued to Stevens on Dec. 23, 1969, both of which are hereby incorporated herein by reference. While these catheters have good torquing and kink resistant properties, it was soon realized that catheters of this type needed to have an extremely soft tip so as to reduce trauma to the portions of the vessel coming in contact with the tip.

Typically, a separate soft tip, made from softer plastics and not having a reinforcing braid, is fused to the body of the catheter. However, this method of making a soft tip catheter is expensive in that it requires additional time and labor to fuse the tip onto the catheter. For catheter sheath introducers, this manufacturing step is often prohibitively expensive. Catheter sheath introducers generally do not have a reinforcing braid layer so that the soft tip can be integral to the body of the catheter. Catheter sheath introducers are usually tapered and thinner at their tip so that they are softer. However, it would be advantageous to have a braided catheter sheath introducer for improved kink resistance and torque control. For some procedures, a braided sheath introducer may eliminate the need for a guiding catheter.

Therefore, there has been a need to provide a catheter which has a soft tip which is integral with the body of the catheter and does not have to be separately fused thereon. Such a catheter would reduce the manufacturing cost of guiding catheters and the like, and make it possible to manufacture an affordable braided catheter sheath introducer. Accordingly, the present invention provides an improved fuseless soft tipped catheter and a method of making the same.

SUMMARY OF THE INVENTION

In accordance with the present invention, there is provided a catheter having an elongated tubular body with a distal end, a proximal end and at least one lumen extending therebetween. The body is made from three layers of extruded plastic which adhere to each other. The body has an inner and outer layer made from a polymer, and a middle layer also made from a polymer. The middle layer is more flexible and has a lower melt temperature than the inner and outer layers. The catheter further includes an integral fuseless distal tip. The distal tip is made from the middle layer and no more than one of the inner and outer layers. The distal tip is softer than portions of the body proximal thereto.

In accordance with another aspect of the present invention, there is provided a method of making a fuseless soft tip tubular catheter, of the type described above. The method involves first providing at least one polymer material for forming the inner and outer layers for the tubular body and providing another polymer material for forming the middle layer of the tubular body. The middle layer polymer material is more flexible and has a lower melting temperature than the inner and outer layer polymer materials. The middle layer is capable of adhering to the inner and outer layers. The method then involves extruding the catheter so as to form the tubular body having the inner, outer and middle layers. Thereafter, at least the distal end of the catheter is heated so as to form a distal tip. The distal tip is made from the middle layer and no more than one of the inner and outer layers. The distal tip is softer than portions of said body proximal thereto.

BRIEF DESCRIPTION OF THE DRAWINGS

While the specification concludes with claims which particularly point out and distinctly claim the subject matter forming the present invention, it is believed that the invention will be better understood from the following description of the preferred embodiment taken in conjunction with the accompanying drawings wherein:

DETAILED DESCRIPTION OF THE INVENTION

Figure 1:
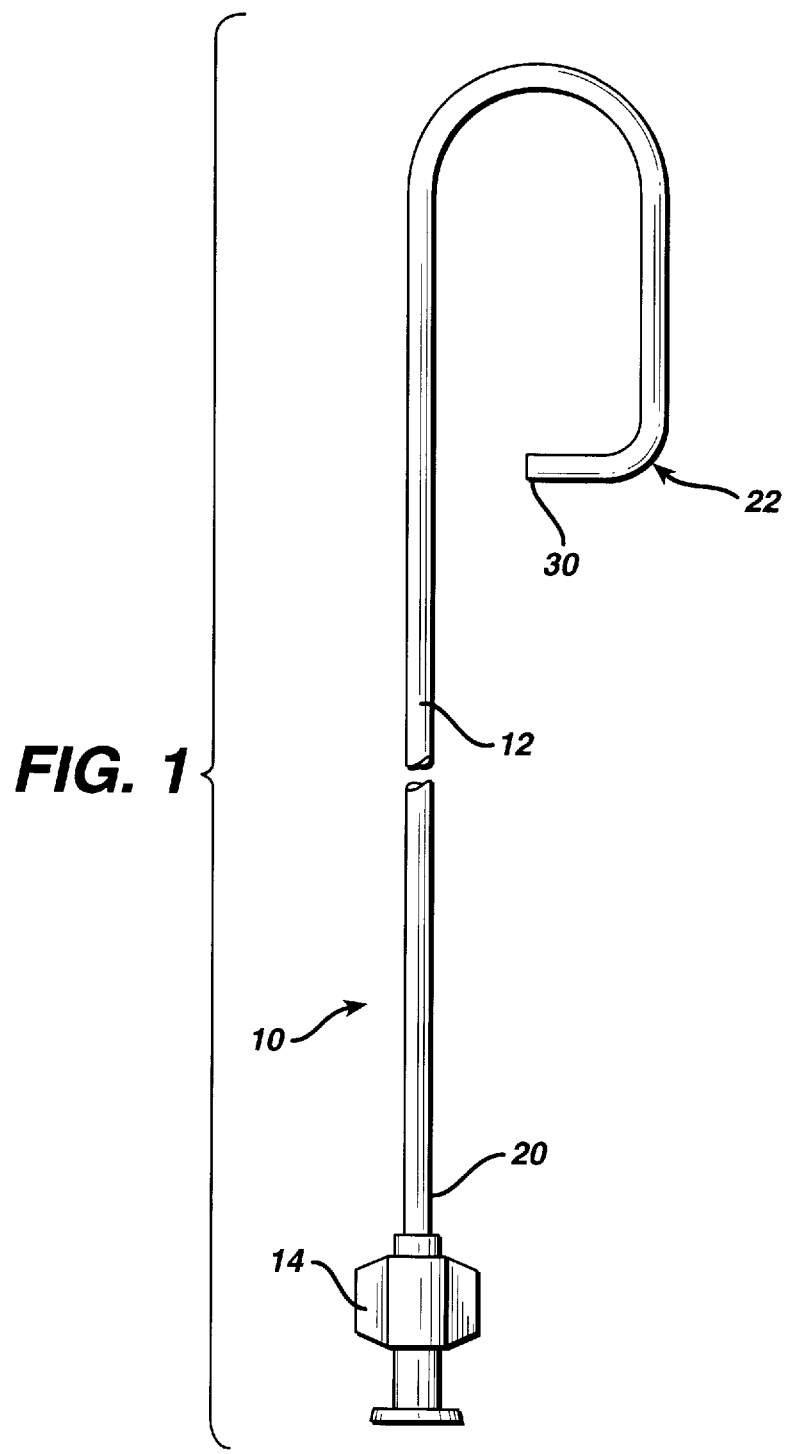
FIG. 1 is a plan view of an intervascular catheter in accordance with the present invention.

Referring to the drawings wherein like numerals indicate the same elements throughout the views, there is shown in FIG. 1 a catheter 10 in accordance with the present invention. Catheter 10 has an elongated tubular body 12 with a proximal end 20, a distal end 22 and at least one lumen 34 extending therebetween. FIG. 1 shows a guiding catheter in accordance with the present invention, however, as will be appreciated by those skilled in the art, the present fuseless soft tip catheter, and method of making the same, can equally be applied to diagnostic catheters, catheter sheath introducers, etc. Catheter 10 includes a hub 14 of conventional design as found on most guiding catheters. Hub 14 would be replaced with a hemostasis valve when applying the present invention to catheter sheath introducers.

Figure 2:
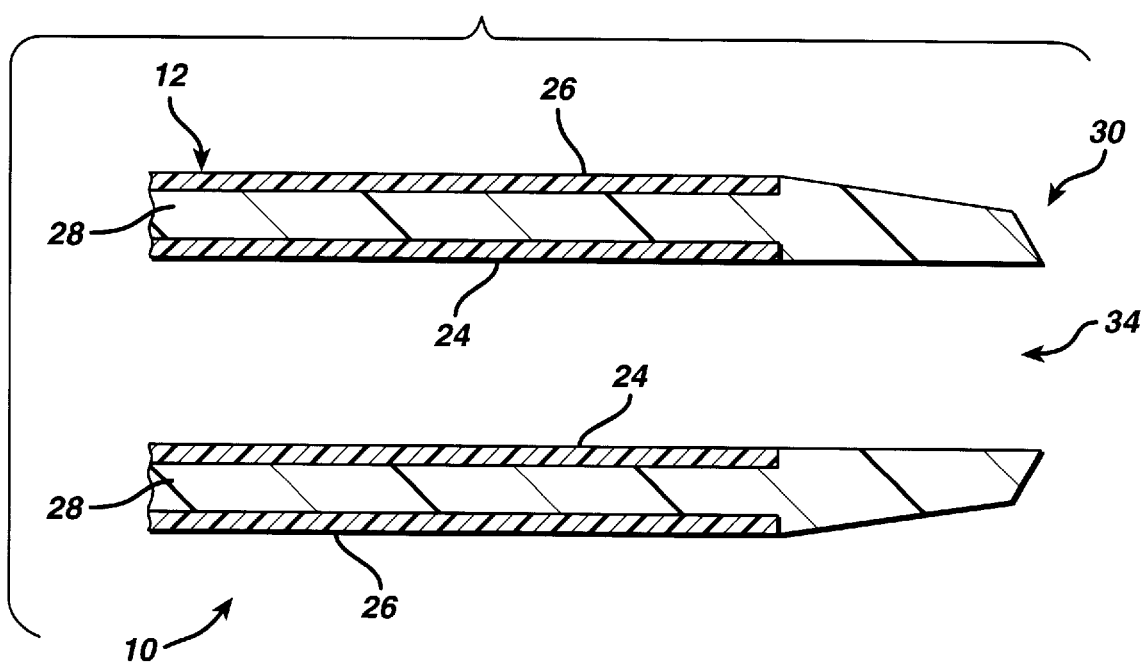
FIG. 2 is a simplified cross-sectional view of the soft distal tip of the catheter shown in FIG. 1.

Body 12 is best described by referring to FIG. 2. As seen from that figure, body 12 is made from three layers of extruded plastic which adhere to each other. The body has an inner layer 24, an outer layer 26 and a middle layer 28. Layers 24, 26 and 28 are all made from a polymers. The inner and outer layers are preferably made from what is sometimes referred to by those skilled in the art as a semi-rigid polymer. Examples of these include: polyamides, polyamide elastomers, copolymers based on polyamides such as Pebax 7033 (available from Atochem, Paris, France and Philadelphia, Pa.), high-density polyethylene, rigid polyurethane, and polypropylene. Inner layer 24 may further include a lubricity enhancing agent mixed with the polymer. Such lubricity enhancing agents are well known in the art including: mineral fillers such as bismuth oxychloride, mica, graphite and silicone or hydrogel materials such as polyvinylpyrrolidone. The middle layer is made from a polymer which is more flexible and has a lower melt temperature than the inner and outer layers. Examples of suitable materials for middle layer 28 include: low-durometer polyurethane, low density polyethylene, maleated polyolefins such as Plexar® (available from Quantum Chemical, Cincinnati, Ohio), nylon elastomers, Pebax 2533® (available from Atochem), copolymers of nylon-11 and other polyamides.

Catheter 10 further includes an integral fuseless distal tip 30. Distal tip 30 is made from a distal portion of middle layer 28 which extends distally of body 12. Distal tip 30 may also include either a portion of inner layer 24 or outer layer 26 which extends distally of body 12. However, most preferably, distal tip 30 is made only from middle layer 28. Because the distal tip is made from the middle layer and no more than one of the inner and outer layers, it is softer than portions of the body 12 proximal thereto. Distal tip 30 can be tapered inwardly towards said lumen for easy insertion into a vessel, such as when applying the invention to a catheter sheath introducer.

Middle layer 28 may also include a reinforcing braid wire imbedded therein. Such a braid wire is discussed in the hereinbefore incorporated Stevens patents. However, as discussed later herein, the braid wire preferably does not extend into distal tip 30. Middle layer 28 may also include a radiopaque agent mixed with the polymer. Suitable radiopaque agents are well known in the art such as bismuth subcarbonate and barium sulfate. If the inner and outer layers are made from a radiolucent material, and tip 30 comprises only the distal most portion of middle layer 28, the catheter will have what is referred to as a bright tip. The advantages of bright tip catheters are set forth in U.S. Pat. No. 5,171,232 issued to Castillo et al. on Dec. 15, 1992, which is hereby incorporated herein by reference.

In accordance with another aspect of the present invention, there is provided a method of making a fuseless soft tip tubular catheter, of the type described above. After the appropriate materials for the inner, outer and middle layers are chosen, the tubular body is formed by extruding the three layers together to form the body. Such extrusion techniques are well known to those of ordinary skill in the art. Thereafter, at least the distal end of the catheter is heated so as to form a distal tip 30, described above.

Figure 3A:
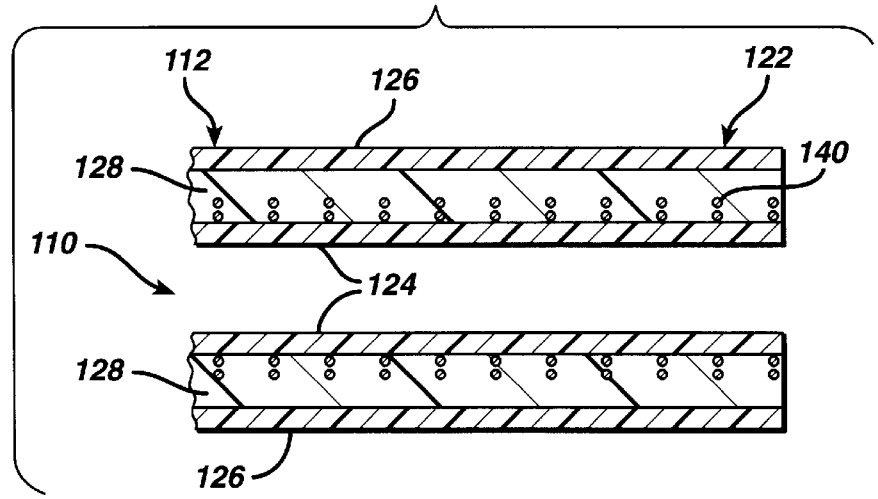
FIGS. 3A–3C are simplified cross-sectional views of a distal end of a catheter made in accordance with the present invention, showing the catheter at various manufacturing stages.
Figure 3B:
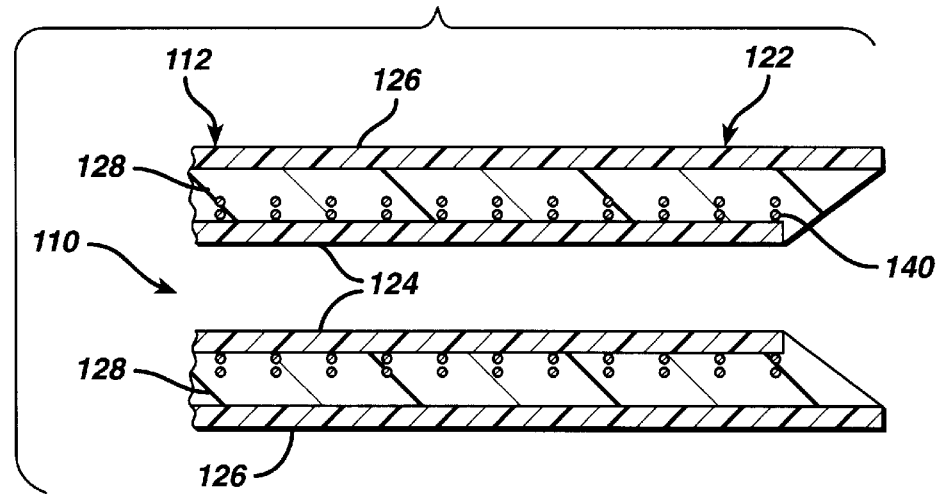
Figure 3C:
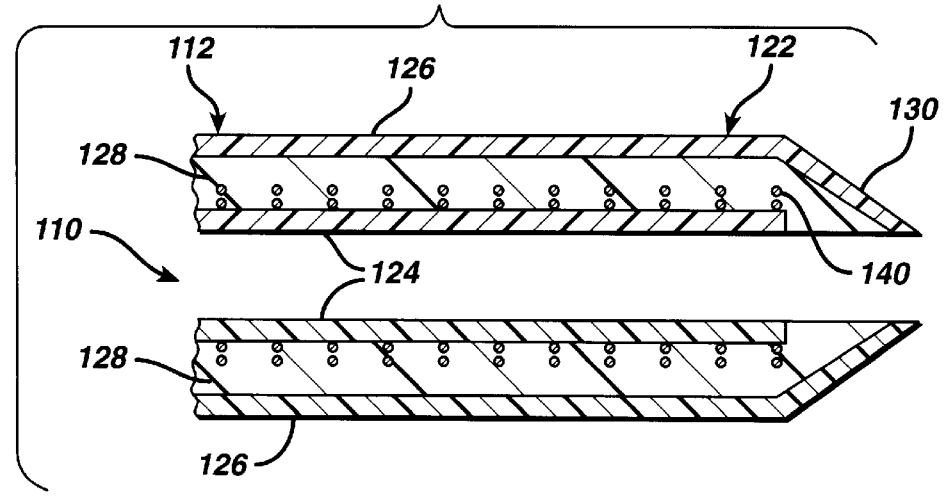

A simplified cross-sectional view of a catheter made in accordance with the present invention is shown in FIGS. 3A to 3C. Those figures show the distal end 122 on of a body 112 of catheter 110 made in accordance with the present invention. Body 112 is made from three layers of extruded plastic which adhere to each other. The body has an inner layer 124, an outer layer 126 and a middle layer 128, all of which are made of the same or similar materials as those for catheter 10 described above, wherein the middle layer is made from a polymer which is more flexible and has a lower melt temperature than the inner and outer layers. Catheter 110 also includes a layer of braided wire 140.

After the inner layer is extruded, the braid layer is placed over it, as disclosed in the hereinbefore incorporated Stevens patents, and then the middle and outer layers are extruded over the braided inner layer. The distal end of the body 112 now appears as it does in FIG. 3A. The catheter is then annealed at sufficient times and temperatures, above the melting temperature of the middle layer but below the melting temperature of the inner and outer layers. As the catheter is annealed, the middle layer begins to melt and flow distally, often dragging the outer layer with it. The catheter 110 now appears as it does in FIG. 3B. The distal end of the catheter is then inserted into a die or mold and heated so that it appears as it does in FIG. 3C, which shows the soft distal tip 130 of catheter 110.

Figure 4:
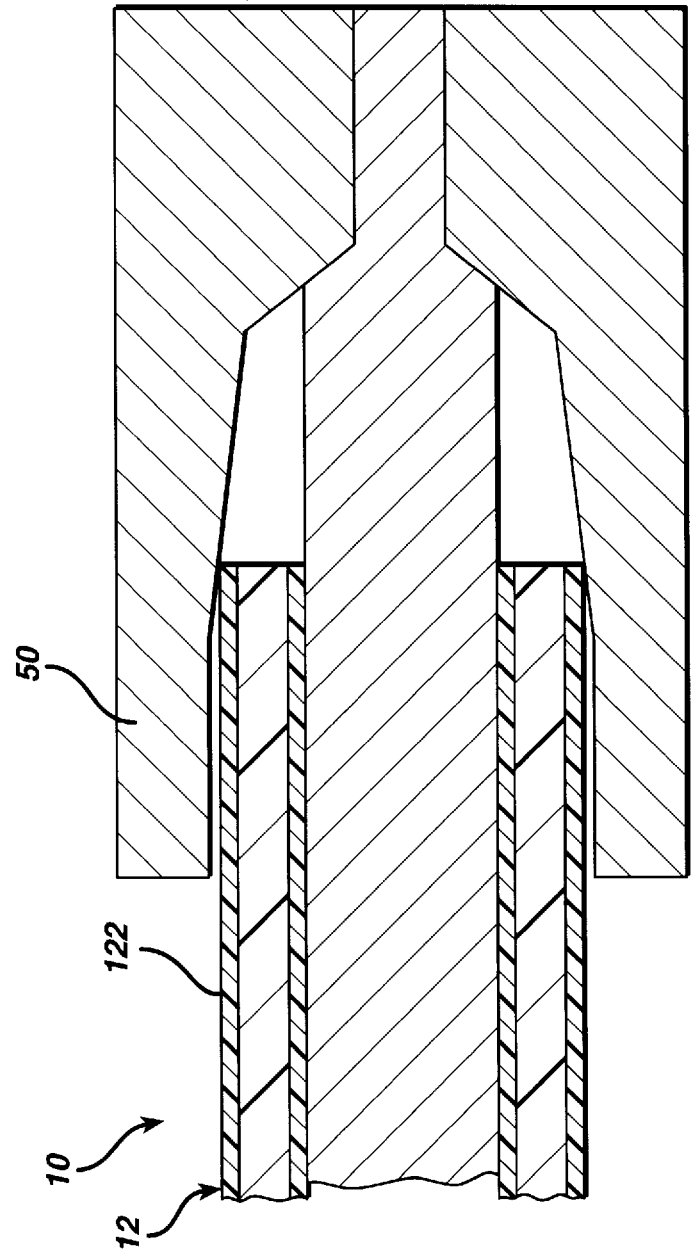
FIG. 4 is a simplified cross-sectional view of the distal end of the catheter shown in FIG. 1, as it is being inserted into a tip forming die.

However, the annealing process does not need to be performed to make the soft distal tip in accordance with the present invention. FIG. 4 shows catheter 10 after it has been extruded. Upon extrusion, the catheter is inserted into die 50 and heated above the melting temperature of the middle layer but below the melting temperature of the inner and outer layers. This causes the middle layer to flow distally, so as to form the soft tip 30 shown in FIG. 2.

The method of making a fuseless soft tip catheter in accordance with the present invention, can be illustrated in the following Examples.

EXAMPLE

A braided catheter is made using Nylon 12 as the inner and outer layers. A maleated polyolefin sold by Quantum Chemical (Cincinnati, Ohio) under the name Plexar®, also referred to as an adhesive resin or tie-layer resin, is used for the middle layer. The catheter includes a 0.001 inch diameter braid wire imbedded within the Plexar. The inner layer is extruded over a silver coated copper mandrel and collected in a spool. The spool is transferred to a high speed 16 Carrier braiding machine (such as the DF16A braiding machine commercially available from Sprika, a division of Hacoba, Japan) which braids the wire over the base coat. Thereafter, the braided inner layer is taken back to the extrusion line and the middle and outer layers are extruded thereon at the same time.

Samples are cut to a length of 4 inches and placed in an oven at 130° for 30 minutes. The samples are allowed to cool to room temperature. The samples increase in length on average 0.090 inches. The outer layer of both ends of the samples extend distally of the inner layer. Moreover, the middle layer remains attached to both layers so that the middle layer extends distally of the inner layer as well. After the samples are allowed to cool, they are placed in a mold similar to the one shown in FIG. 4. The mold is heated to about 200° F. and the tips of the samples are pushed into the mold, thereby forming a catheter similar to that shown in FIG. 3C.

Although particular embodiments of the present invention have been shown and described, modification may be made to the catheter without departing from the spirit and scope of the present invention. The terms used in describing the invention are used in their descriptive sense and not as terms of limitations.

What is claimed is:

1. A method of making a fuseless soft tip tubular catheter, the catheter having an elongated tubular body, a distal end, a proximal end, and at least one lumen extending therebetween, said method comprising the steps of:

(a) providing at least one polymer material for forming an inner and outer layer for the tubular body;

(b) providing another polymer material for forming a middle layer of the tubular catheter, said middle layer polymer material being more flexible and having a lower melting temperature than said inner and outer layer polymer materials, said middle layers being capable of adhering to said inner and outer layers;

(c) extruding the tubular catheter so as to form the tubular body comprising said inner, outer and middle layers, (d) heating the distal end of the tubular catheter to a temperature above the melting temperature of the polymer material forming said middle layer and below the melting temperature of the polymer materials forming said inner and outer layers, and flowing said middle layer distally so as to form a distal tip comprising said middle layer and no more than one of said inner and outer layers, so that said distal tip is softer than portions of the tubular body proximal thereto.

2. The method according to claim 1 wherein said inner, outer and middle layers are selected from the group consisting of polyamides, polyamide elastomers and copolymers of polyamides.

3. The method according to claim 1 wherein the inner and outer layers are selected from the group consisting of maleated polyolefins, high-density polyethylene, rigid polyurethane, and polypropylene.

4. The method according to claim 1 wherein the middle layer is selected from the group consisting of low-durometer polyurethane, low density polyethylene, and maleated polyolefins.

5. A method of making a fuseless soft tip tubular braided catheter, the catheter having an elongated tubular body, a distal end, a proximal end, and at least one lumen extending therebetween, said method comprising the steps of:

(a) providing at least one polymer material for forming an inner and outer layer for the tubular body;

(b) providing another polymer material for forming a middle layer of the tubular catheter, said middle layer polymer material being more flexible and having a lower melting temperature than said inner and outer layer polymer materials, said middle layers being capable of adhering to said inner and outer layers, (c) extruding said inner layer, braiding a wire around said inner layer and extruding said middle and outer layers around said wire so as to form the tubular body comprising said inner, outer and middle layers;

(d) heating the distal end of the tubular catheter to a temperature above the melting temperature of the polymer material forming said middle layer and below the melting temperature of the polymer materials forming said inner and outer layers, and flowing said middle layer distally so as to form a distal tip comprising said middle layer and no more than one of said inner and outer layers, so that said distal tip is softer than portions of the tubular body proximal thereto.

6. The method according to claim 5 wherein said inner, outer and middle layers are selected from the group consisting of polyamides, polyamide elastomers and copolymers of polyamides.

7. The method according to claim 5 wherein the inner and outer layers are selected from the group consisting of maleated polyolefins, high-density polyethylene, rigid polyurethane, and polypropylene.

8. The method according to claim 5 wherein the middle layer is selected from the group consisting of low-durometer polyurethane, low density polyethylene, and maleated polyolefins.

* * * * *